United States Patent [19]

Sitte et al.

[11] Patent Number: 5,181,443
[45] Date of Patent: Jan. 26, 1993

[54] DEVICE FOR CONTROLLING THE DRIVE AND FORWARD FEED OF MICROTOMES, PARTICULARLY ULTRAMICROTOMES

[76] Inventors: Hellmuth Sitte, Reitherspitzstrasse 166, A-6100 Seefeld, Austria; Helmut Hässig, Am Gedünner 21; Armin Kunz, Uhlandstrasse 19, both of D-6650 Homburg-Saar, Fed. Rep. of Germany; Klaus Neumann, Eichenstrasse 8, D-6652 Bexbach-Saar 5, Fed. Rep. of Germany

[21] Appl. No.: 682,955

[22] Filed: Apr. 10, 1991

[30] Foreign Application Priority Data

Apr. 11, 1990 [AT] Austria .................................. 873/90

[51] Int. Cl.⁵ ............................ G01N 1/06; B26D 5/20
[52] U.S. Cl. ............................... 83/72; 83/414; 83/703; 83/915.005
[58] Field of Search ................... 83/72, 76, 703, 410, 83/915.5, 414

[56] References Cited

U.S. PATENT DOCUMENTS 3,785,234  1/1974  Sitte ........................ 83/414
4,377,958  3/1983  Leighton .................. 83/412
4,484,503  11/1984 Sitte et al. ................ 83/717
4,625,608  12/1986 Behme et al. ............ 83/713

FOREIGN PATENT DOCUMENTS 0822000  4/1981  U.S.S.R. .................. 83/915.5

Primary Examiner—Hien H. Phan
Attorney, Agent, or Firm—Wenderoth, Lind & Ponack

[57] ABSTRACT

A device for controlling the drive and forward feed of a microtome, particularly an ultramicrotome, includes a driving motor for moving a specimen or knife and a servomotor for generating a forward feed of the specimen towards an edge of the knife or vice versa. A high travelling speed of the specimen needed for rapid initial cutting is coupled to a high rate of forward feed. One single switching operation is performed, for instance, by a snap-engaging step switch via relay switches. The driving motor and the servomotor can be simultaneously switched over to pairs of values which correspond to subsequent rough cutting and ultra-thin cutting. Individual values for cutting speed and forward feed are separately preselected, readjusted, and read from a display. Selected program stages are indicated by signals.

16 Claims, 1 Drawing Sheet

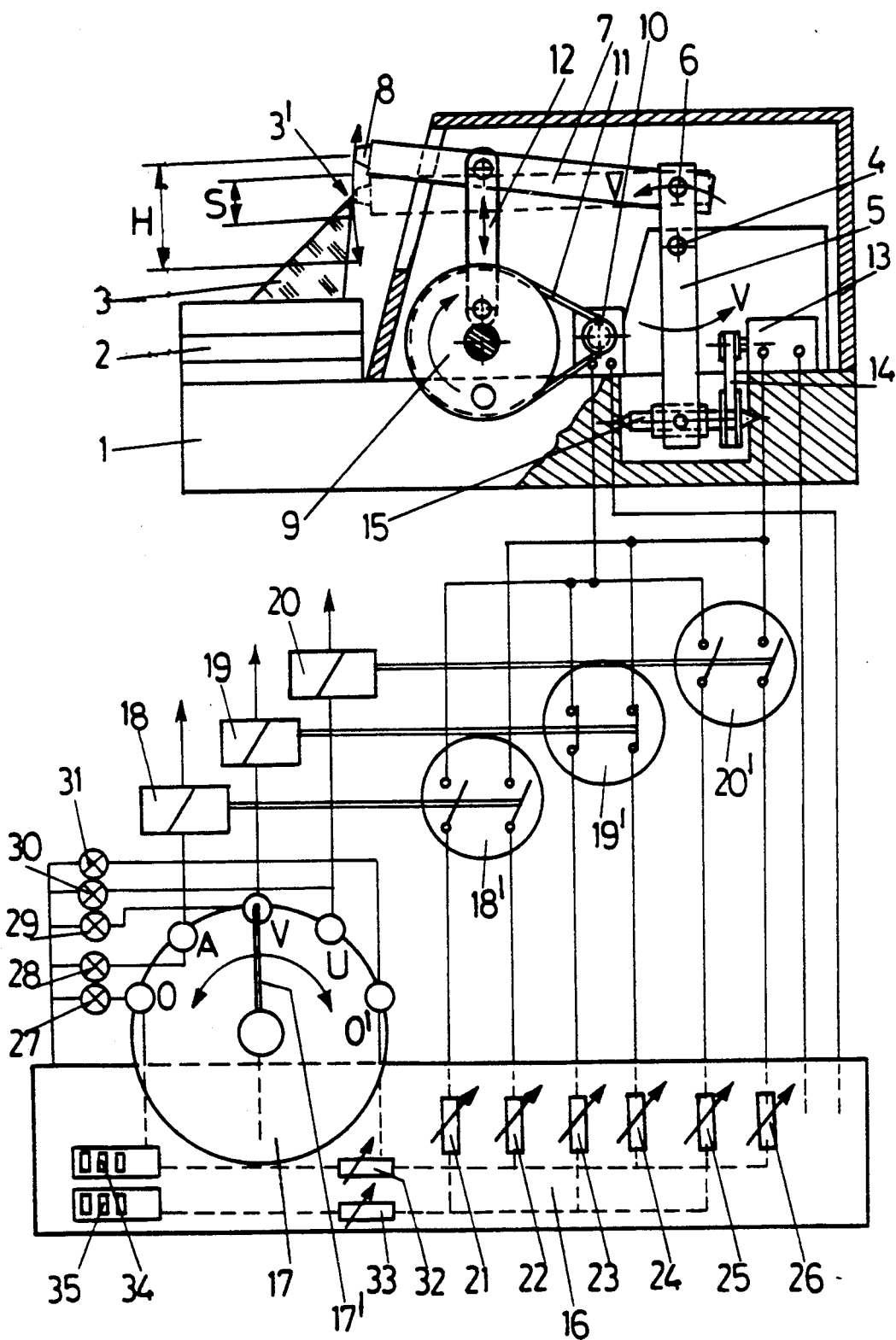

DEVICE FOR CONTROLLING THE DRIVE AND FORWARD FEED OF MICROTOMES, PARTICULARLY ULTRAMICROTOMES

BACKGROUND OF THE INVENTION

The invention relates to a device for controlling the drive and feed of a microtome, particularly an ultramicrotome, with a driving motor for moving a specimen or a knife and with at least one servomotor for advancing the specimen towards the knife or vice versa.

According to the state of the art, microtomes, particularly ultramicrotomes, generally comprise at least two motor drives of which at least one serves as a servomotor for advancing a specimen towards a knife or vice versa by amounts which correspond to whatever sectioning thicknesses have been preselected, while the other motor drive serves as a driving motor for relative movement of the specimen with respect to the fixed knife or, vice versa, of the knife in relation to the fixed specimen (Cutting Movement; cf. the nature of section preparation, inter alia H. Sitte, Ultramikrotomie, mta-Journal Extra No. 10, Umschau-Verlag, Breidenstein GmbH, Frankfurt 1982). As a rule, before commencing a section preparation, the cutting edge of the knife is brought as close as possible to the specimen or object, or conversely the object is moved as close as possible to the cutting edge of the knife, although direct contact of the object with the knife edge is avoided since this may well result in damage to the object and to the knife edge. Afterwards, particularly in the case of ultramicrotomes of the type described above, the motor drive is switched on and the object or the knife is moved at a relatively high speed and the knife is advanced at a relatively great rate of feed towards the object, or alternatively the object is advanced towards the knife until such time as a first section fragment is produced. Since, with regard to efficiency of preparation, it is desirable to make this first cut as rapidly as possible, the object or the knife is in this case moved at the greatest possible speed (e.g. 100 mm/sec) on its path, and generally one forgoes the alternating drive which is usual during normal operation, particularly with ultramicrotomes, and during which whichever part is moving is moved slowly for cutting (e.g. 1 to 5 mm/sec) but is returned at a higher travelling speed (e.g. 10 to 20 mm/sec). Similarly, even with ultramicrotomes, until such time as the first section fragment has been taken by the knife, a comparatively high rate of forward feed is chosen (e.g. about 2 μm per cycle), the "cycle" constituting one complete movement pattern from one cutting process to the next cutting process in sequence. Accordingly, by a greatly abbreviated cycle time (e.g. about 1 sec/cycle) and a high rate of forward feed per cycle (e.g. about 2 μm/cycle) it is possible to achieve a rapid approximation of knife and object (e.g. about 2 μm/sec or 0.12 mm/min) so that cutting can be started in the fastest possible way. However, this procedure makes it necessary, immediately after the first section fragment has been taken from the object, to reduce both the travelling speed of the moving part and also the rate of forward feed to levels which reliably exclude the possibility of damage to the object or to the knife edge. In ultramicrotomy, this object is served in that the travelling speed of the moving part is reduced to about 5 mm/sec while the rate of forward feed is reduced to about 0.5 μm. Certainly, this requires both measures being adopted without delay since both too high a travelling speed and also too great a thickness of section resulting from an excessively high rate of forward feed per cycle will in themselves already produce damage to the object (e.g. tearing, splitting and fragmentation) and the knife (scoring of the knife, portions of the sensitive knife blade may be broken away). If one also takes into account the delay due to the limited capacity of the user for reaction, then the result is an extremely critical situation which can often result in damage, stress-related operating errors and finally the result that one either forgoes the theoretical possibility of rapid progress of operation or risks damage or that one switches off the motor drive completely in order calmly to adjust the new travelling speed and the new rate of forward feed. Often, after the interruption in operation which is mentioned above as the final alternative, one comes to the conclusion that after such an interruption in operation the results can no longer be reproduced since such an interruption alters the situation, for example by reason of added flexible specimens.

The problems described above are generally repeated when, after a number of cycles, the entire cutting area has been completely broached. One is then again confronted by the problem of reducing the rate of forward feed to the value for those section thicknesses which one requires, for example for electron microscopic operations (e.g. section thicknesses of around 0.05 μm/cycle). Since these are less rigid in the range of extremely thin sections usual in ultramicrotomy, as section in the rage of micromillimeter thicknesses, then in this case also the travelling speed of the moving element, in the area of ultramicrotomy of the moving object, must at the same time be substantially reduced (for instance to 0.5 mm/sec). In this case also, a delayed reduction in travelling speed may lead to a more pronounced compaction of a section which often necessitates a complete interruption in section preparation or shut-down of the motor drive so that the compacted sections can be removed from the cutting edge of the knife. Therefore, this secondary arrangement also requires considerable dexterity and may often lead to problems if the operator is not skillful.

SUMMARY OF THE INVENTION

Therefore, the object of the invention is to provide an easily operated device for controlling the drive and rate of advance of a microtome, particularly an ultramicrotome, and which without special practice or skill on the part of the operator and without any delay or other problems caused by interruption in operation can rapidly and reliably produce the desired sections.

According to the invention, this is achieved in that a switching device which can be actuated by a switching element is provided for simultaneously changing the values of cutting speed produced by the driving motor and rate of feed of the specimen towards the knife and brought about by the servomotor, or vice versa.

In the case of the device according to the invention, by one single setting operation a switching process synchronously alters both the travelling speed of the moving part (cutting speed) and also the rate of advance per cycle or the sectioning thickness, whatever may be the preset levels of travelling speed and cutting thickness, as these are preselected at separate and quite independent elements, for example digitally, so that there is no need for a separate adjustment of these two vital parameters at a changeover.

A development of the invention may reside in that a rotary knob, lever or sliding member used for control purposes snaps into engagement at each program stage corresponding to a pair of values representing cutting speed and rate of feed so that "blind operation" becomes possible, whereby an operator can devote full attention to observing the cutting process. In this respect, it is a good idea if the displays of operating data valid at any given moment, such as for example cutting speed and rate of feed (cutting thickness) are fed into an observation instrument, particularly a stereo microscope.

In a different kind of development of the invention, the same effect can be achieved in that by a pressure on a button and via an electronic unit or a relay, it is possible to change over to the next "program stage", in other words the next pair of values for cutting speed and rate of feed, a second push button providing for a return to the preceding program stage.

According to a further development of the invention, in addition to the program stages for rapid cutting, for rough cutting the specimen block and for producing sections for light or electron microscopic investigation, empty stages are provided as first and/or last program stages during which the drive is either stationary or continues to run as far as a preset or preselectable point, and subsequently whichever part is moving remains in this position and during this stoppage of whichever is the moving part, the advance feed movement is likewise stationary.

Within the framework of such a control arrangement it is for example advantageous if, after switch-on, through the transition from an empty stage to a first program stage for a first pair of values other than zero for cutting speed and rate of feed, firstly the moving part moves at a very high speed just as a knife and object are guided toward each other at a high rate of forward feed per cycle, whereas after the first section fragment has been produced, within the framework of the next program stage in succession, both the travelling speed of whichever is the moving part and also the rate of forward feed are reduced. A further reduction in both values takes place at that moment when the cutting area of the specimen block has been rough cut. In the manner explained above, this third setting serves for producing the sections needed for light or electron optical observation. Once the necessary number of sections have been taken, one passes from this stage, for example by onwards rotation of a rotary switch, to the next empty stage in succession. When this happens, the moving part either stops at once or moves on to a position which is particularly favorable for the taking of specimens. Once the sections have been prepared, one switches back to the last program stage and there is no compulsion initially to work at a high speed and then at an average speed and, via these stages, to arrive back at the pair of values chosen for the taking of sections.

A further development of the invention may reside in that a visual display signals whatever position has been reached in the "program", for instance by light emitting diodes of different color and/or spatial disposition. Similarly, whatever speeds and rates of feed have been preselected can also be shown in a display. A particular advantage in this respect is achieved by the already mentioned mixing of the image into an observation instrument, for example a stereo microscope.

Finally, a further development of the invention may reside in the fact that at two elements, for example two rotary potentiometers, whichever values are preselected in the program for speed and rate of feed can be altered within a range predetermined for each program stage and so adapted for optimum compliance with the special conditions of each individual operation. In a simplified development, this adjustment may be restricted to a pair of values which are of particular significance for the preparation of the section, and in the case of an ultramicrotome this will for example be the range for production of ultra-thin sections.

In the case of an alternating drive in which the moving part is moved slowly for cutting but at a high travelling speed for a return movement (the alternating drive itself possibly being controlled in per se known manner, for example as a function of an angle encoder or a light barrier on a drive shaft), by means of the switching arrangement according to the invention it is possible to vary in synchronism not only the rate of feed and the actual cutting speed simultaneously but also the associated return speed or any intermediate speeds which might be required. Therefore, one specific rate of feed is always correlated to a specific pattern of travelling speed of the moving part.

BRIEF DESCRIPTION OF THE DRAWING

Further advantages and features of the invention will emerge from the ensuing description of a preferred example which is shown in the accompanying drawing which is a roughly diagrammatically simplified view of an ultramicrotome and a diagram of an example of circuit thereof.

DETAILED DESCRIPTION OF THE INVENTION

The ultramicrotome shown diagrammatically in the attached drawing is of essentially conventional type (concerning the design and function of ultramicrotomes see inter alia H. Sitte, Ultramikrotomie, mta-Journal extra No. 10, Umschau Verlag, Breidenstein GmbH, Frankfurt 1983 and H. Sitte and K. Neumann, Ultramikrotomie und apparative Hilfsmittel der Ultramikrotomie, in: G. Schimmel and W. Vogell, Methodensammlung der elektronemikroskopie, Wissenschaftliche Verlags GmbH, Stuttgart 1983). Mounted on a base 1 there is, on one side thereof, a cruciform support 2 with a knife 3 and, on an opposite side thereof, a bearing 4 on which is articulated a reduction lever 5 which, in turn and via a bearing 6, supports a specimen carrier bar 7 with a specimen or object 8. The specimen carrier bar 7 can be caused to perform a reciprocating upwards and downwards movement by rotation of a hand wheel 9, or by means of a driving motor 10 via a transmission 11, and a control lever 12, the specimen 8 performing a travelling stroke H. If the instrument is equipped with an alternating drive control (control elements not shown in the drawing), the specimen 8 is, during its downwards movement and in region S ("cutting window"), propelled at a reduced travelling speed for the taking of sections, whereas during the rest of its travel it is guided at a higher "return speed". During the downwards movement, sections are taken at a cutting edge 3'. of the knife 3 when the specimen carrier bar 7 is advanced in the direction of an arrow V, i.e. toward knife 3. This feed movement is brought about, for instance, by a servomotor 13 (e.g. a stepping motor), which via a transmission 14 rotates a micrometer spindle 15 which engages the bottom end of the lever 4. A control device of the invention as described and discussed in detail hereinabove may comprise, for example, an electronic control unit 16 having connected thereto a step-by-step switch 17 having contacts or steps "O-A-V-U-O'", a switching contact 17' being capable of being rotated in a clockwise direction through the contacts O<←A<←V<←U<←O'. An advantageous variation may be for the two extreme positions of the step-by-step switch to be connected to each other so that it is possible to turn the switch through 360° in both directions and to make the contacts the sequence O→>A→>V→>U→>O'>. . . or vice versa . . . O'<←O<←A<V<←U<←O'. To the contacts A, V and U are connected relays 18, 19 and 20 that actuate switching contacts 18', 19' and 20' when the switching contact 17' of the step switch 17 engages the switching contact A (relay 18), V (relay 19) or U (relay 20) connected to the appropriate relay. The switching contacts 18', 19' and 20' are of two-core construction and therefore are capable of simultaneously connecting the driving motor 10 which is connected by one core and the servomotor 13 connected by the other core to the control unit 16. At the control unit, setting elements 21 to 26 are, for example, six rotary potentiometers or digital elements of which the elements 21, 22 and 23 are provided, for instance, to preselect the cutting speeds in the cutting area S of the preparatory stroke H by the driving motor 10, and the elements 24, 25 and 26 to preselect the stepwise advance of the specimen toward the knife by the servomotor 13. Finally, a number of signal lamps 27 to 31 (e.g. light emitting diodes) are connected to the switching contacts O-A-V-U-O' of the step switch 17/17, and they indicate whichever "program stage" is set:

In accordance with the description already given, for example, setting element 21 is adjusted to set (program stage "A") to a specimen speed of 100 mm/sec, while setting element 22 is set to a specimen speed of 5 mm/sec for rough cutting (program stage "V"), and the element 23 for ultra-thin cutting (program stage "U") is set to a specimen speed of 0.5 mm/sec. The corresponding values for rate of feed are preselected by the elements 24, 25 and 26 in the same way, for example at 2 μm (A), 0.5 μm (V) and 0.05 μm (U). At the commencement of operation, the switching contact 17' of the step switch 17 is moved from position 0 to position A ("Set"). The signal lamp 27 goes out, the signal lamp 28 shows that the position A is reached, the relay 18 closes the contact 18' the motor 10 moves the specimen for instance at a speed of 100 mm/sec in single drive and the servomotor 13 advances the specimen 8 at 2 μm per cycle towards the knife edge 3'. Since the cycle time is very short under these working conditions (e.g. 1 second), the specimen 8 is advanced very rapidly (e.g. at 2 μm/sec or 0.12 mm/min) stepwise towards the knife edge 3'. Once the first section fragment has been taken, the step switch 17/17' is moved on by one notch to the position V for rough cutting the cutting area. The signal 28 goes out and the signal 29 associated with the contact V is illuminated. The relay 18 opens the switching contact 18' and the relay 19 closes the switching contact 19' as is shown for example in the drawing. In synchronism, the motor drive 10 switches over to a movement during which the specimen 8 in the cutting zone S is moved at 5 mm/sec and in each cycle it is advanced stepwise by the servomotor 13 by 0.5 μm towards the knife 3. The instrument remains in this operating mode until the cutting area has been completely rough cut. When this situation is achieved, the rotary contact 17' is rotated on to the next position U for ultra-thin cutting. The signal 29 goes out and the signal 30 associated with the contact U lights up. At the same time, the relay 19 releases the contacts of the switch 19' and the relay 20 connected to the contact U closes the contacts of the switch 20'. The drive moves the specimen 8 now at 0.5 mm/sec.

The servomotor advances the specimen 8 at 0.05 μm per cycle towards the knife edge 3'. Once sufficient sections have been taken, the switching contact 17' is moved to the position 0' which is indicated by the signal 31 becoming illuminated. Once the sections have been prepared, the operation is continued by the step switch 17/17' being turned back to position U when the pair of values 0.5 mm/sec and 0.05 μm per cycle are restored. Should it prove, for example, that the thickness of cutting is possibly too low or the travelling speed is perhaps somewhat too high, then both values can be readjusted independently of each other by adjusting elements 33 (cutting speed) and/or 32 (forward feed). Whichever preselected or corrected values are currently applicable by virtue of the programming will appear at displays 34/35.

The system according to the invention can be accomplished in various combinations and using various elements according to the varying designs of microtomes, particularly ultramicrotomes, and varying needs in the specialized fields of operation, without in any way sacrificing the characteristics of the invention. For example, this is true for the operation of two servomotors, one for the object and one for the advance movement instead of the servomotor 13 which is described by way of example. It is immaterial how may contacts a step switch has in comparison with the step switch 17/17' and whether the connection to the implementing means is made directly or via relays. Finally, for implementing the idea underlying the invention it is immaterial how the switch-over takes place and how the selected pair of values is adjusted and corrected and what implementing means produce the drive and the feed, so long as these movements are brought about by electric motors.

We claim:

1. A control device for controlling the operation of a microtome, particularly an ultramicrotome, wherein a specimen and a knife are relatively moved to cut sections from the specimen, said control device comprising:

a driving motor for moving one of the knife and the specimen at a cutting speed to cut sections from the specimen;

at least one servomotor for advancing at least one of the knife and the specimen toward the other at a rate of feed to regulate the thickness of the section cut from the specimen; and means for simultaneously changing both the value of said cutting speed produced by said driving motor and the value of said rate of feed produced by said at least one servomotor, said changing means comprising a switching arrangement operatively associated both with said driving motor and with said at least one servomotor and actuatable by a switching element for changing said values.

2. A device as claimed in claim 1, wherein said switching arrangement includes means defining plural switching conditions each corresponding to a respective pair of said value of said cutting speed and said value of said rate of feed.

3. A device as claimed in claim 2, further comprising adjusting means for selectively preadjusting each said value of said pair of values for each switching condition.

4. A device as claimed in claim 2, further comprising means for operating said switching element to transition in a first direction in a predetermined sequence among said plural switching conditions.

5. A device as claimed in claim 4, wherein said operating means comprises a push button.

6. A device as claimed in claim 4, further comprising reversing means for operating said switching element to transition in a second direction opposite to said first direction.

7. A device as claimed in claim 6, wherein said reversing means comprises a push button.

8. A device as claimed in claim 1, wherein said switching arrangement includes a switching condition in which both said driving motor and said at least one servomotor are inoperative, said switching condition being restorable upon continuous onward switching of said switching element.

9. A device as claimed in claim 1, wherein said switching element comprises a switch having plural contacts and a lever connectable selectively with said contacts.

10. A device as claimed in claim 9, wherein said lever is a slidable member.

11. A device as claimed in claim 9, wherein said switch and contacts are movable.

12. A device as claimed in claim 1, wherein said switching arrangement comprises a plurality of relays actuatable independently by said switching element, and each said relay actuates simultaneously a respective switching contact connected to said driving motor and a respective switching contact connected to said at least one servomotor.

13. A device as claimed in claim 12, further comprising means for presetting respective different said values for each of said relays.

14. A device as claimed in claim 13, further comprising means for adjusting preset values of said rate of feed of selected said relays.

15. A device as claimed in claim 14, further comprising means, operable independently of said rate of feed adjusting means, for adjusting preset values of said cutting speed of selected said relays.

16. A device as claimed in claim 13, further comprising means for adjusting preset values of said cutting speed of selected relays.

* * * * *